(12) United States Patent
Powers et al.

(10) Patent No.: US 8,961,570 B2
(45) Date of Patent: Feb. 24, 2015

(54) SPINAL CORRECTION SYSTEM AND METHOD

(75) Inventors: Alison Powers, Memphis, TN (US); Chris Johnson, Germantown, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 227 days.

(21) Appl. No.: 13/357,376

(22) Filed: Jan. 24, 2012

(65) Prior Publication Data

US 2013/0190824 A1    Jul. 25, 2013

(51) Int. Cl.
*A61B 17/88* (2006.01)

(52) U.S. Cl.
USPC ............................................ 606/278

(58) Field of Classification Search
USPC ................................ 606/246–279
See application file for complete search history.

(56) References Cited

U.S. PATENT DOCUMENTS

| | | | |
|---|---|---|---|
| 6,287,308 B1 | 9/2001 | Betz et al. | |
| 6,296,643 B1 | 10/2001 | Hopf et al. | |
| 6,709,438 B2 | 3/2004 | Dixon et al. | |
| 6,783,527 B2 | 8/2004 | Drewry et al. | |
| 7,771,475 B2 | 8/2010 | Michelson | |
| 7,909,826 B2 | 3/2011 | Serhan et al. | |
| 2002/0120270 A1* | 8/2002 | Trieu et al. | 606/61 |
| 2003/0088251 A1 | 5/2003 | Braun et al. | |
| 2007/0213823 A1 | 9/2007 | Trieu | |
| 2007/0244562 A1 | 10/2007 | Conner et al. | |
| 2008/0009866 A1 | 1/2008 | Alamin et al. | |
| 2008/0294263 A1* | 11/2008 | Altarac et al. | 623/17.16 |
| 2009/0012614 A1 | 1/2009 | Dixon | |
| 2009/0030462 A1* | 1/2009 | Buttermann | 606/249 |
| 2009/0198287 A1* | 8/2009 | Chiu | 606/301 |
| 2009/0264932 A1 | 10/2009 | Alamin et al. | |
| 2011/0184471 A1 | 7/2011 | Foley et al. | |
| 2011/0196494 A1 | 8/2011 | Yedlicka et al. | |

OTHER PUBLICATIONS

NuNec Cervical Arthroplasty System.

* cited by examiner

*Primary Examiner* — Mary Hoffman
*Assistant Examiner* — Tara R Carter

(57) ABSTRACT

A fusionless correction system comprises a longitudinal element extending between a first end and second end. At least one fixation element is disposed with the longitudinal element and is configured for disposal in bone. A lock is disposed with the at least one fixation element and includes at least one bone penetrating projection. The lock is movable relative to the at least one fixation element between a first non-engaging configuration and a second engaging configuration such that the at least one bone penetrating projection extends beyond an outer surface of the at least one fixation element. Methods of use are disclosed.

20 Claims, 4 Drawing Sheets

SPINAL CORRECTION SYSTEM AND METHOD

TECHNICAL FIELD

The present disclosure generally relates to medical devices for the treatment of musculoskeletal disorders, and more particularly to a surgical system and method for fusionless correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be elective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, for stabilization of a treated section of a spine. This disclosure describes an improvement over these prior art technologies.

SUMMARY

Accordingly, a surgical system and method for fusionless correction of a spine disorder is provided. In one embodiment, in accordance with the principles of the present disclosure, a fusionless correction system is provided. The system comprises a longitudinal element extending between a first end and second end. At least one fixation element is disposed with the longitudinal element and is configured for disposal in bone. A lock is disposed with the at least one fixation element and includes at least one bone penetrating projection. The lock is movable relative to the at least one fixation element between a first non-engaging configuration and a second engaging configuration such that the at least one bone penetrating projection extends beyond an outer surface of the at least one fixation element.

In one embodiment, the system comprises a tether extending between a first end and second end. The tether is configured to extend over a plurality of vertebral levels. A plurality of bone dowels are configured for disposal in a spaced apart orientation along the vertebral levels. Each bone dowel defines an opening configured for disposal of the tether such that the tether is movable relative to the dowels. Each bone dowel is configured for implantation with a cavity formed in bone. Each bone dowel defines a longitudinal axis and includes a transverse lock. The lock includes a plurality of bone penetrating projections. Each bone dowel is expandable between a first non-engaging configuration and a second engaging configuration whereby the lock is rotated relative to the bone dowel such that the bone penetrating projections extend beyond an outer surface of the bone dowel to engage a tissue surface of the respective bone cavity.

In one embodiment, a method for fusionless correction of a spine disorder is provided. The method comprises the steps of: providing access to a surgical site adjacent a selected section of a spine; providing a longitudinal element extending between a first end and second end; providing at least one fixation element disposed with the longitudinal element, the at least one fixation element including a lock, the lock including at least one bone penetrating projection; implanting the at least one fixation element in bone; and moving the lock relative to the at least one fixation element such that the at least one bone penetrating projection extends beyond an outer surface of the at least one fixation.

BRIEF DESCRIPTION OF THE DRAWINGS

The present disclosure will become more readily apparent from the specific description accompanied by the following drawings, in which.

Like reference numerals indicate similar pans throughout the figures.

DETAILED DESCRIPTION

Figure 1:
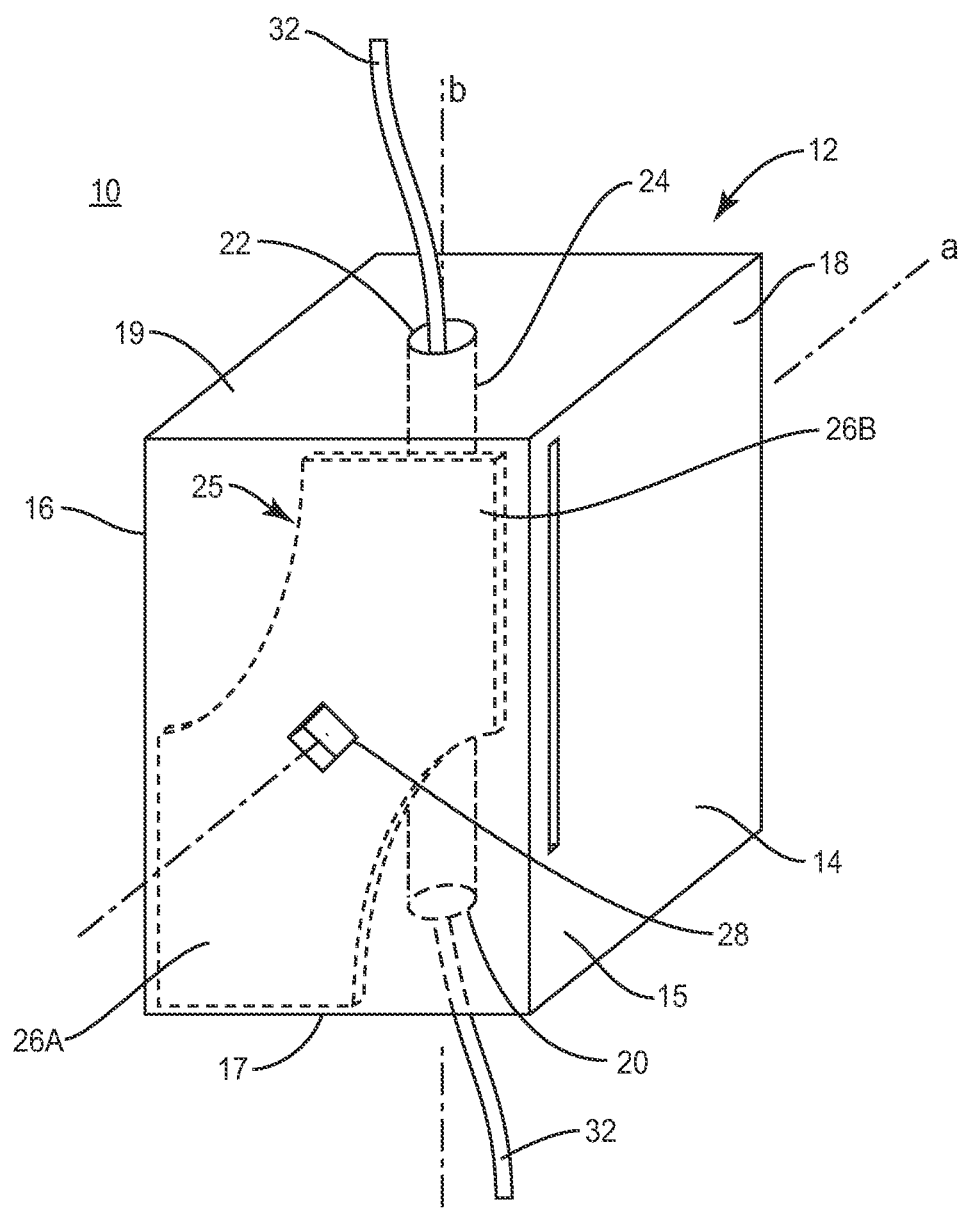
FIG. 1 is a perspective view of one embodiment of components of the system in accordance with the principles of the present disclosure.
Figure 2:
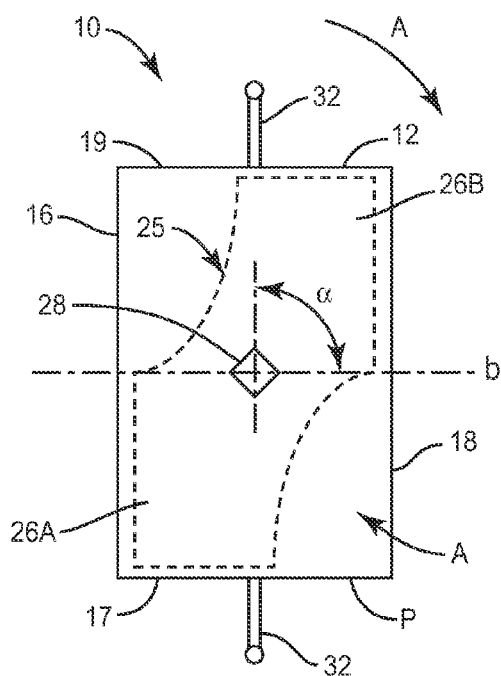
FIG. 2 is a plan view of the components of the system shown in FIG. 1.
Figure 3:
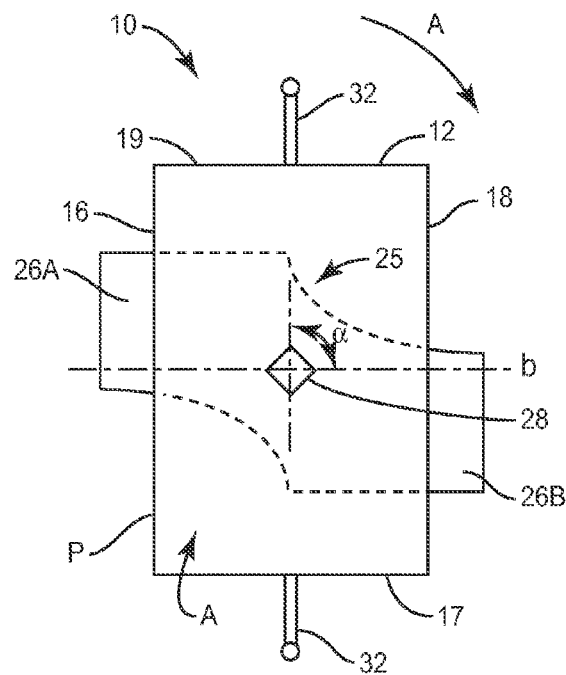
FIG. 3 is a plan view of the components of the system shown in FIG. 1.

The exemplary embodiments of the surgical system and related methods of use disclosed are discussed in terms of medical devices for the treatment of musculoskeletal disorders and more particularly, in terms of a surgical system and method for fusionless correction of a spine disorder. It is envisioned that the surgical system and method may be employed in applications such as fusionless correction of deformities such as scoliosis. For example, the surgical system and method can include attachment of a tether to a convex side of a spine that is curved due to scoliosis. It is contemplated that while the tether may be affixed to a first side of each of a plurality of vertebrae to prevent growth of vertebrae of the first side, the system allows for growth and adjustments to a second side of the plurality of vertebrae.

In one embodiment, the system and method include a lock employed with an oblong-shaped bone dowel/anchor for a more secure deployment under a cortical wall. The lock can use a cam mechanism that results in a larger footprint of the anchor. In one embodiment, the cam lock expands the footprint of the dowel so as to hold it more securely under the cortical shell. This configuration prevents backout of the dowel/anchor. In one embodiment, the system and method are employed as a fusionless tether bone anchor dowel allograft lock. In one embodiment, the system and method relate to a fusionless method for correcting scoliosis using a bone dowel anchoring mechanism that can be made of a biologic material, such as bone, and a flexible member such as a tether made from various materials, for example, a biologic material, such as a tendon or ligament and/or a synthetic polymer. The dowel can anchor the flexible member into an anterior column of vertebrae. The anchor mechanism can include an internal locking/expanding mechanism that is actuated after initial implantation to further hold the dowel in vertebrae under a cortical wall. It is envisioned that actuation of the anchor mechanism does not interfere with the tether.

In one embodiment, the system includes at least one fixation element that affixes a tether material to bone. For example, such tethers or tether material may be used to apply tension on the convex side or lateral side of a spine that has scoliosis by connecting adjacent vertebrae. As a patient grows, the tether material applies a force to straighten the spine.

In one embodiment, the at least one fixation element comprises a bone dowel that utilizes a rotating member and/or cap that lodges into surrounding bone after a rectangular or oblong shaped dowel is inserted into a hole in the bone. The tether is inserted through bone in the dowel prior to the insertion of the dowel into vertebrae. The cap is rotated ninety degrees, for example, to lock the dowel in place adjacent and underneath a cortical shell of vertebrae.

It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical system, such as, for example, a fusionless correction system 10 in accordance with the principles of the present disclosure.

The components of correction system 10 can be fabricated from biologically acceptable materials suitable for medical applications, including metals, synthetic polymers, ceramics and bone material and/or their composites, depending on the particular application and/or preference of a medical practitioner. For example, the components of correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of correction system 10 may have material composites, including the above materials, to achieve various desired characteristics such as strength, rigidity, elasticity, compliance, biomechanical performance, durability and radiolucency or imaging preference. The components of correction system 10, individually or collectively, may also be fabricated from a heterogeneous material such as a combination of two or more of the above-described materials. The components of correction system 10 may be monolithically formed, integrally connected or include fastening elements and/or instruments, as described herein.

Correction system 10 is employed, for example, with an open, mini-open or minimally invasive surgical technique to attach a longitudinal element to a first side, such as, for example, a convex side of a spine that has a spinal disorder. The longitudinal element may be affixed to the convex side of each of a plurality of vertebrae to prevent growth of vertebrae of a selected section of the spine. Correction system 10 allows for growth and adjustments to a second side, such as, for example, a concave side of the plurality of vertebrae for a correction treatment to treat various spine pathologies, such as, for example, adolescent idiopathic scoliosis and Scheuermann's kyphosis.

Correction system 10 includes a flexible longitudinal element, such as, for example, a flexible tether 32 that extends between a first end 34 and a second end 36. Tether 32 has a flexible configuration, which includes movement in a lateral or side to side direction and prevents expanding and/or extension in an axial direction upon fixation with vertebrae, as will be described. It is envisioned that all or only a portion of tether 32 may have a semi-rigid, rigid or elastic configuration, and/or have elastic properties such that tether 32 provides a selective amount of expansion and/or extension in an axial direction. It is further envisioned that tether 32 may be compressible in an axial direction. Tether 32 can include a plurality of separately attachable or connectable portions or sections, such as bands or loops, or may be monolithically formed as a single continuous element. In one embodiment, correction system 10 includes two tethers. It is contemplated that tether 32 is configured to extend over one or a plurality of vertebral levels.

Tether 32 can have a uniform thickness/diameter. It is envisioned that tether 32 may have various surface configurations, such as, for example, rough, threaded fir connection with surgical instruments, arcuate, undulating, porous, semi-porous, dimpled, polished and/or textured according to the requirements of a particular application. It is contemplated that the thickness defined by tether 32 may be uniformly increasing or decreasing, or have alternate diameter dimensions along its length. It is further contemplated that tether 32 may have various cross section configurations, such as, for example, oval, oblong, triangular, rectangular, square, polygonal, irregular, uniform, non-uniform, variable and/or tapered.

It is contemplated that tether 32 may have various lengths, according to the requirements of a particular application. It is further contemplated that tether 32 may be braided, such as a rope, or include a plurality elongated elements to provide a predetermined force resistance. It is envisioned that tether 32 may be made from autograft and/or allograft, as described above, and be configured for resorbable or degradable applications. In one embodiment, the longitudinal element is a cadaver tendon. It is envisioned that tether 32 may include a cadaver ligament, solid core, tubular element, an artificial strand or a flexible rod.

A fixation element, such as, for example, a dowel 12 is configured for disposal, such as, for example, implantation within a cavity formed in tissue, such as, for example, bone. Dowel 12 includes a body 14 having an outer surface 15. Dowel 12 has a length extending along longitudinal axis a. Body 14 is configured for disposal in tissue and outer surface 15 is configured for engagement with tissue. It is envisioned that correction system 10 may include one or a plurality of fixation elements.

Dowel 12 has a rectangular cross section configuration. Body 14 has a substantially rectangular cross-sectional area A, which defines a perimeter P of body 14 along outer surface 15. Outer surface 15 includes side surfaces 16, 17, 18, 19 that define perimeter P of body 12. It is contemplated that other engaging structures may be located on dowel 12, such as, for example, a nail configuration, barbs, raised elements and/or spikes to facilitate engagement of dowel 12 with tissue, such as, for example, vertebrae. It is envisioned that all or only a portion of dowel 12 may have alternate cross section configurations, such as, for example, circular, oval, oblong, triangular, square, polygonal, irregular, uniform, non-uniform, offset, staggered, undulating, arcuate, cage, variable and/or tapered. It is contemplated that outer surface 15 may include one or a plurality of openings. It is contemplated that all or only a portion of outer surface 15 may have alternate surface configurations to enhance fixation with tissue such as, for example, rough, arcuate, undulating, mesh, porous, semi-porous, dimpled and/or textured according to the requirements of a particular application. It is envisioned that all or only a portion of dowel 12 may be disposed at alternate orientations, relative to axis a, such as, for example, transverse, perpendicular and/or other angular orientations such as acute or obtuse, co-axial and/or may be offset or staggered. It is further envisioned that all or only a portion of dowel 12 may be cannulated.

Side surfaces 17, 19 define openings 20, 22, respectively. Openings 20, 22 are disposed in alignment along an axis b, which is disposed transverse to axis a. It is envisioned that axis b may be disposed in various orientations relative to axis a, such as, for example, transverse, perpendicular and/or other angular orientations such as acute or obtuse, co-axial and/or may be offset or staggered. Openings 20, 22 are in communication along a passageway 24. It is envisioned that openings 20, 22 may be separate and spaced apart. Openings 20, 22 and passageway 24 are configured for disposal of tether 32 such that tether 32 is movable relative to dowel 112.

Dowel 12 includes a transverse lock 25 disposed with body 14. Lock 25 has substantially planar faces and is rotatable relative to body 14 to a engage a tissue surface of a bone cavity. In one embodiment, lock 25 is connected and/or attached with outer surface 15. In one embodiment, lock 25 is disposed within a cavity of body 14, for example, recessed below outer surface 15 or disposed within a slot. It is envisioned that lock 25 may be connected and/or attached with body 14 via a fastening elements, such as for example, shafts, rods, wedges, buttons, clips, snaps, fittings, rivets, staples, nails, adhesives, fixation plates and/or posts. It is envisioned that body 14 may include one or a plurality of locks.

Lock 25 includes a first bone penetrating projection, such as, for example, a spike 26A and a second bone penetrating projection, such as, for example, a spike 26B. Spike 26A is oriented in a first direction and spike 26B is oriented in a second direction, which is opposite to the first direction. Spikes 26A, 26B are movable in a transverse orientation relative to axis a. Spikes 26A, 26B are disposed 180 degrees apart. It is envisioned that the spikes may be disposed at other relative angular orientations, such as, acute or obtuse. It is contemplated that the bone penetrating projection may have various engaging structures, such as, for example, a nail configuration, serrated, textured, staggered, uneven, undulating, smooth, barbs and/or raised elements to facilitate engagement with tissue, such as, for example, a cortical wall of vertebrae. In one embodiment, lock 25 includes serrated and or textured surfaces such that spikes 26A, 26B are movable in a first direction and lock 25 includes a biasing member that resists movement of spikes 26A, 26B in a second direction, opposite to the first direction. This configuration facilitates rotation of spikes 26A, 26B in the first direction and into a locked position under a cortical shell and minimizes the risk of inadvertent reverse rotation of spikes 26A, 26B in the second direction. It is further contemplated that spikes 26A, 26B may engage and catch or rest with a bone or tissue surface but not penetrate a bone or tissue surface. It is envisioned that lock 25 may include one or a plurality of bone penetrating projections.

Lock 25 includes a pin 28 extending along axis a that includes a socket configured for engagement with a tool or instrument for rotating lock 25 and spikes 26A, 26B. Lock 25 is mounted within body 14 with pin 28 adjacent axis a for rotational movement of spikes 26A, 26B relative to body 14. Body 14 defines a cavity, such as, for example, a slot 42 (FIGS. 5 and 6) that allows lock 25 to rotate freely therein. Slot 42 extends such that lock 25 can rotate through an angle α, in the direction shown by arrow A in FIGS. 2 and 3. It is contemplated that angle α is 90 degrees, however, may alternatively be in a range of 0 through 180 degrees. It is further contemplated that lock 25 may be rotated in a clockwise or counter-clockwise direction.

Lock 25 is rotatable relative to body 12 and expandable between a first, non-engaging configuration (FIG. 3) such that spikes 26A, 26B are disposed within perimeter P, and a second, engaging configuration (FIG. 4) such that at least a portion of spikes 26A, 26B extend beyond outer surface 15 and perimeter P to engage a tissue surface, such as, for example, vertebral tissue adjacent a cortical wall of a bone cavity, such, for example, a cavity in a vertebra. It is contemplated that the depth or length of spike 26A and/or 26B that extends beyond outer surface 15 may be varied depending on the requirements of a particular application, such as, the depth of penetration into a bone or tissue surface and/or the accessible body space. In one embodiment, lock 25 may be rotated in an opposing direction to release dowel 12 from penetrating engagement with tissue and allow for readjustment and/or repositioning.

In one embodiment, a plurality of dowels 12 may be configured for disposal in a spaced apart orientation along a plurality of vertebral levels such that tether 32 extends over a plurality of vertebral levels. It is contemplated that this configuration positions dowels 12 under a cortical shell of a vertebra to secure correction system 10 with selected vertebrae. In one embodiment, dowels 12 are disposed consecutively at each vertebral level. In one embodiment, dowels 12 are disposed at one or a plurality of alternating vertebral levels.

In assembly, operation and use, correction system 110, similar to the system described above, is employed with a surgical procedure, such as, for a correction treatment to treat adolescent idiopathic scoliosis and/or Scheuermann's kyphosis of a spine. It is contemplated that one or all of the components of correction system 10 can be delivered or implanted as a pre-assembled device or can be assembled in situ. Correction system 10 may be completely or partially revised, removed or replaced.

Figure 4:
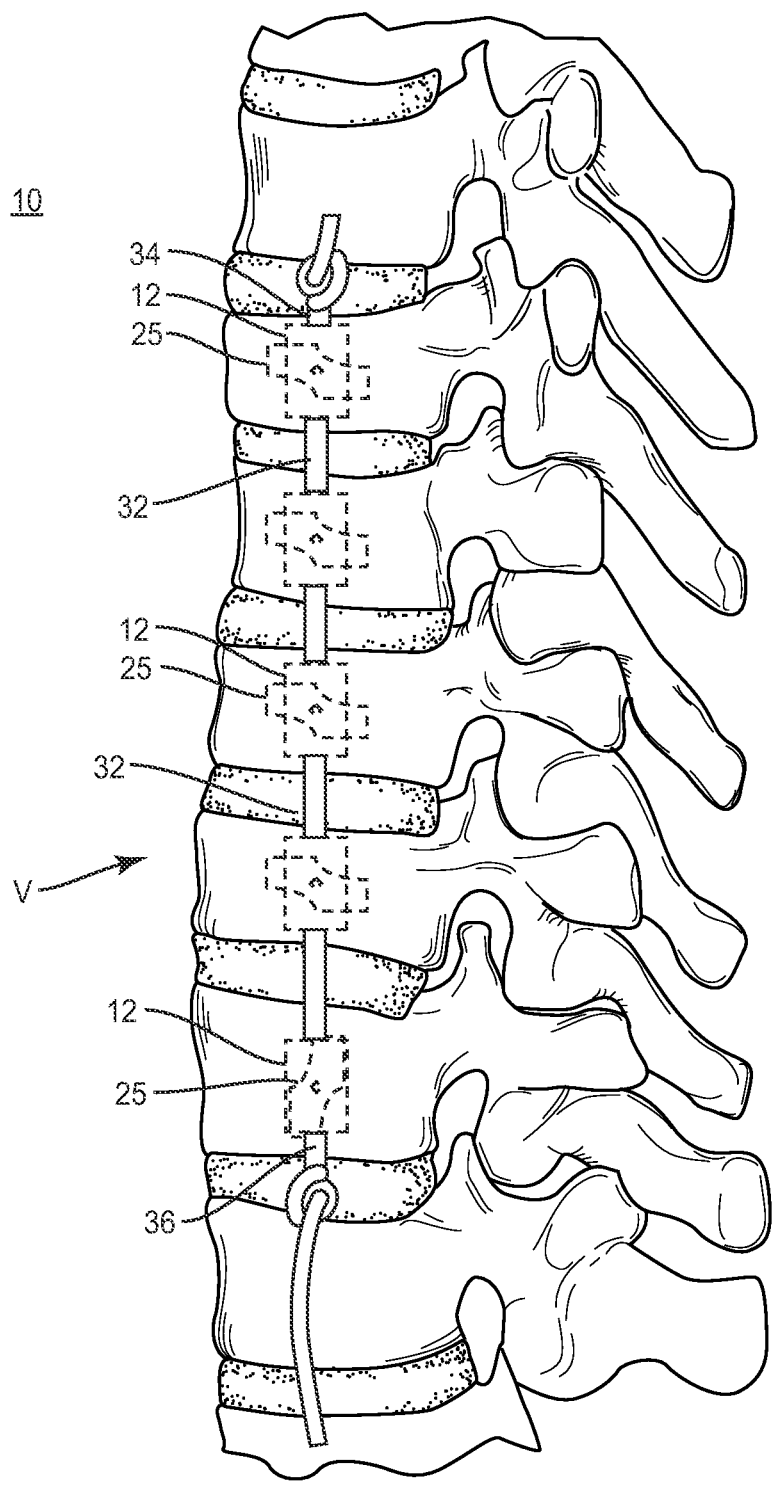
FIG. 4 is a perspective view of the components of the system shown in FIG. 1 engaged with vertebrae.
Figure 5:
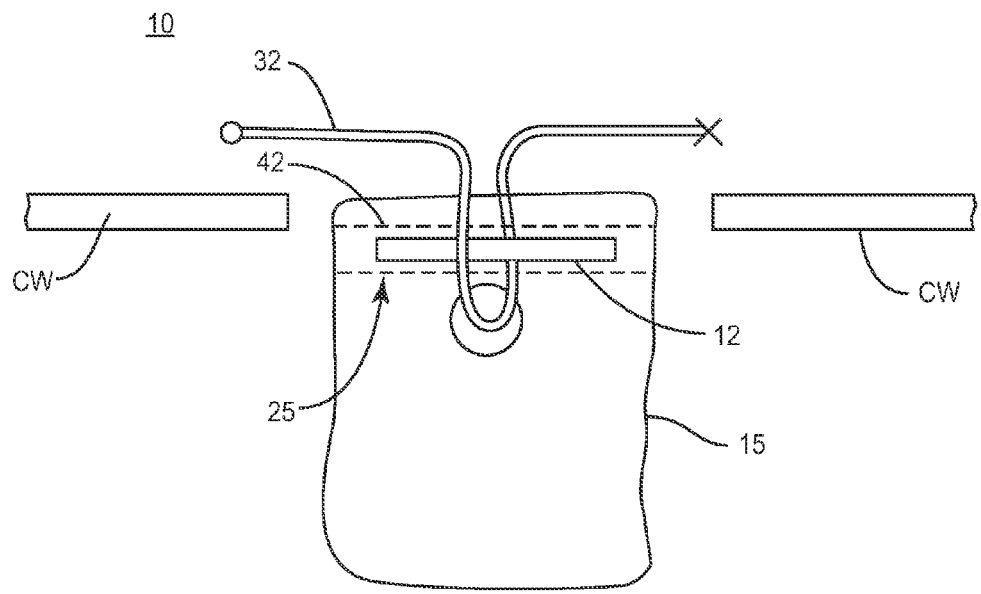
FIG. 5 is a side view of the components of the system shown in FIG. 1 engaged with vertebrae.
Figure 6:
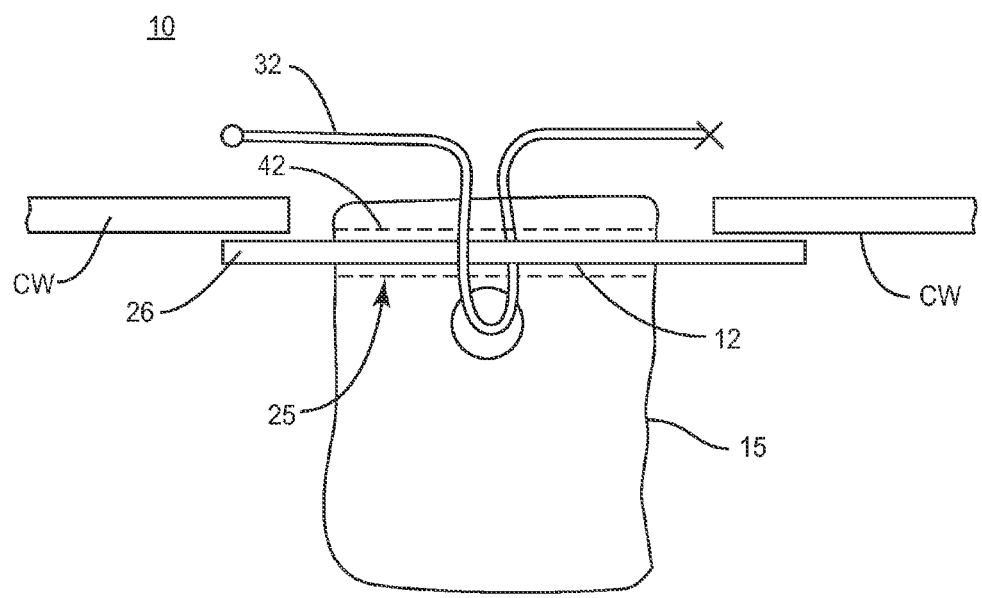
FIG. 6 is a side view of the components of the system shown in FIG. 1 engaged with vertebrae.

For example, as shown in FIGS. 4-6, correction system 10, described above, can be employed with a surgical correction treatment of an applicable condition or injury of an affected section of a spinal column and adjacent areas within a body, such as, for example, vertebrae V. It is envisioned that correction system 10 may be employed with one or a plurality of vertebrae.

In use, to treat vertebrae V, a medical practitioner obtains access to a surgical site including vertebrae V in any appropriate manner, such as through incision and retraction of tissues. It is envisioned that correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder. The configuration and dimension of tether 32 is determined according to the configuration and dimension of a selected section of vertebrae V and the requirements of a particular application.

An incision is made in the body of a patient and a cutting instrument (not shown) creates a surgical pathway for implantation of components of correction system 10. A preparation instrument (not shown) can be employed to prepare tissue surfaces of vertebrae V, as well as for aspiration and irrigation of a surgical region according to the requirements of a particular surgical application.

Pilot holes are made in selected vertebra of vertebrae V for receiving dowels 12. Lock 25 is disposed in the first, non-engaging configuration (FIG. 5) such that spikes 26A, 26B are disposed within perimeter P. Dowels 12 are delivered along the surgical pathway adjacent the selected vertebra. Each dowel 12 is inserted or otherwise engaged with a particular vertebra, according to the particular requirements of the surgical treatment.

Other components of correction system 10 are delivered to the surgical site along the surgical pathway(s), for example, tether 32. Tether 32 is disposed with each dowel 12 such that tether 32 is disposed with dowels 12 along vertebrae V. A tool or instrument engages the socket of pin 28 to rotate lock 25 to a second, engaging configuration (FIG. 6) such that at least a portion of spikes 26A, 26B extend beyond outer surface 15 and perimeter P to engage vertebral tissue adjacent a cortical wall CW of a vertebra. This configuration positions dowels 12 under cortical wall CW to secure correction system 10 with a selected section of vertebrae V. Dowels 12 are configured to support a tensile load with tether 32 over a selected section of vertebrae V.

The components of correction system 10 are attached with a first side, such as, for example, a convex side of vertebrae V to prevent growth of a selected section of vertebrae V, while allowing for growth and adjustments to a second side, such as, for example, a concave side of vertebrae V to provide treatment. Compression of the selected section of vertebrae V occurs along the convex side.

In one embodiment, correction system 10 includes an agent, which may be disposed, packed or layered within, on or about the components and/or surfaces of correction system 10. It is envisioned that the agent may include bone growth promoting material, such as, for example, bone graft to enhance fixation of the fixation elements with vertebrae V.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of correction system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of correction system 10. Upon completion of the procedure, the surgical instruments and assemblies are removed and the incision is closed.

It is contemplated that the components of correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of correction system 10 and method of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A fusionless correction system comprising:
a longitudinal element extending between a first end and second end;
at least one fixation element disposed with the longitudinal element and being configured for disposal in bone, the at least one fixation element including a bone dowel; and
a lock disposed with the at least one fixation element and including first and second projections configured to penetrate bone, the projections being fixed relative to one another, wherein the lock is movable relative to the at least one fixation element between a first non-engaging configuration and a second engaging configuration such that the projections extend beyond an outer surface of the at least one fixation element.

2. A fusionless correction system as recited in claim 1, wherein the longitudinal element includes a tether.

3. A fusionless correction system as recited in claim 1, wherein the longitudinal element includes a cadaver tendon.

4. A fusionless correction system as recited in claim 1, wherein the longitudinal element is configured to extend over a plurality of vertebral levels.

5. A fusionless correction system as recited in claim 1, wherein the at least one fixation element includes a plurality of fixation elements configured for disposal in a spaced apart orientation along a plurality of vertebral levels.

6. A fusionless correction system as recited in claim 1, wherein the at least one fixation element is configured for implantation with a cavity formed in the bone.

7. A fusionless correction system as recited in claim 1, wherein the projections expand to engage a tissue surface that defines a cavity formed in the bone.

8. A fusionless correction system as recited in claim 1, wherein the at least one fixation element defines an opening configured for disposal of the longitudinal element.

9. A fusionless correction system as recited in claim 8, wherein the longitudinal element is movable through the opening such that the longitudinal element is movable relative to the at least one fixation element.

10. A fusionless correction system as recited in claim 1, wherein the at least one fixation element defines a cross-sectional area defining a perimeter such that the first configuration includes the projections being disposed within the perimeter and the second configuration includes the projections extending beyond the perimeter.

11. A fusionless correction system as recited in claim 1, wherein the projections are rotatable through an angle of 90 degrees.

12. A fusionless correction system as recited in claim 1, wherein the projections are serrated.

13. A fusionless correction system as recited in claim 1, wherein the first projection is oriented in a first direction and the second projection is oriented in a second direction, opposite to the first direction.

14. A fusionless correction system as recited in claim 1, wherein the at least one fixation element defines a longitudinal axis and the projections are movable in a transverse orientation relative to the longitudinal axis.

15. A fusionless correction system as recited in claim 1, wherein the at least one fixation element includes a socket configured to rotate the projections.

16. A fusionless correction system as recited in claim 1, wherein the longitudinal element includes a flexible tether.

17. A fusionless correction system comprising:
a tether extending between a first end and second end, and being configured to extend over a plurality of vertebral levels; and
a plurality of bone dowels configured for disposal in a spaced apart orientation along the vertebral levels, each bone dowel defining an opening configured for disposal of the tether such that the tether is movable relative to the dowels, each bone dowel being configured for implantation with a cavity formed in bone; and
each bone dowel defining a longitudinal axis and including a transverse lock, the lock including a plurality of projections each configured to penetrate bone, wherein each bone dowel is expandable between a first non-engaging configuration and a second engaging configuration whereby the lock is rotated relative to the bone dowel such that the projections extend beyond an outer surface of the bone dowel to engage a tissue surface of the respective bone cavity.

18. A fusionless correction system as recited in claim 17, wherein the bone dowel defines a cross-sectional area defining a perimeter such that the first configuration includes the projections being disposed within the perimeter and the second configuration includes the projections extending beyond the perimeter.

19. A method for fusionless correction of a spine disorder, the method comprising the steps of:
- providing access to a surgical site adjacent a selected section of a spine;
- providing a longitudinal element extending between a first end and second end;
- providing at least one fixation element disposed with the longitudinal element, the at least one fixation element including a bone dowel having a lock, the lock including first and second projections configured to penetrate bone, the projections being fixed relative to one another;
- implanting the at least one fixation element in bone; and
- moving the lock relative to the at least one fixation element such that the projections extend beyond an outer surface of the at least one fixation.

20. A method as recited in claim 19, wherein the step of moving the lock includes rotating the projections through an angle of 90 degrees.

\* \* \* \* \*